United States Patent [19]

Nabel et al.

[11] Patent Number: 5,460,965
[45] Date of Patent: Oct. 24, 1995

[54] DNA AND RNA ENCODING PROTEINS USEFUL IN THE REGULATION OF KB-CONTAINING GENES, AND CELLS CONTAINING SAME

[75] Inventors: Gary J. Nabel; Roland M. Schmid; Neil D. Perkins, all of Ann Arbor, Mich.

[73] Assignee: The Regents of the University of Michigan, Ann Arbor, Mich.

[21] Appl. No.: 145,138

[22] Filed: Dec. 17, 1993

Related U.S. Application Data

[62] Division of Ser. No. 747,781, Aug. 21, 1991, Pat. No. 5,324,818.

[51] Int. Cl.$^6$ .............................. C12N 5/10; C12N 1/21; C12N 15/12

[52] U.S. Cl. .................... 435/240.2; 435/172.3; 435/252.3; 435/252.33; 536/23.5

[58] Field of Search ................. 536/23.5; 435/240.2, 435/240.4, 252.3, 254.11, 172.3, 252.33

*Primary Examiner*—Richard A. Schwartz
*Assistant Examiner*—Nancy T. Vogel
*Attorney, Agent, or Firm*—Oblon, Spivak, McClelland, Maier & Neustadt

[57] ABSTRACT

Proteins, and corresponding DNA and RNA sequences, useful for the regulation of expression of κB-containing genes are disclosed. These proteins are useful to either stimulate or inhibit the expression of κB-containing genes. Proteins stimulating the expression of κB-containing genes have an amino acid sequence at least 80% identical to the amino acid sequence of from position 1 to position 374 of p100 [SEQ ID NO: 2]. Proteins having an inhibitory effect on the expression of κB-containing genes have sequences either at least 80% identical to the amino acid sequence of from position 407 to the carboxyl end of p100 [SEQ ID NO: 2] or having an amino acid sequence at least 80% identical to the amino sequence of either from position 1 to 100 sor from position 101 to position 374 of p100 [SEQ ID NO: 2].

13 Claims, 6 Drawing Sheets

FIGURE 2

```
         1
p49      M.ESCYNPG. LDGIIEYD.. .DFKLNSSIV .EPKEPAPET ADGPYLVIVE
p100     M.ESCYNPG. LDGIIEYD.. .DFKLNSSIV .EPKEPAPET ADGPYLVIVE
p105     MAEDDPYLGR PEQMFHLDPS LTHTIENPEV FQPQMALP.T ADGPYLQILE
cons.    M E    G           D           V   P  P T ADGPYL I E 51                                                100
p49      QPKQRGFRFR YGCEGPSHGG LPGASSEKGR KTYPTVKICN YEGPAKIEVD
p100     QPKQRGFRFR YGCEGPSHGG LPGASSEKGR KTYPTVKICN YEGPAKIEVD
p105     QPKQRGFRFR YVCEGPSHGG LPGASSEKNK KSYPQVKICN YVGPAKVIVQ
cons.    QPKQRGFRFR Y CEGPSHGG LPGASSEK   K YP VKICN Y GPAK  V 101                                               150
p49      LVTHSDPPRA HAHSLVGKQC SELGICAVSV GPKDMTAQFN NLGVLHVTKK
p100     LVTHSDPPRA HAHSLVGKQC SELGICAVSV GPKDMTAQFN NLGVLHVTKK
p105     LVTNGKNIHL HAHSLVGKHC .EDGICTVTA GPKDMVVGFA NLGILHVTKK
cons.    LVT        HAHSLVGK C  E GIC V  GPKDM    F  NLG LHVTKK 151                                               200
p40      NMMGTMIQKL QRQRLRSRPQ GI......... TEAEQ...RE LEQEAKEL..
p100     NMMGTMIQKL QRQRLRSRPQ GL......... TEAEQ...RE LEQEAKEL..
p105     KVFETLEARM TEACIRGYNP GLLVHPDLAY LQAEGGGDRQ LGDREKELIR
cons.             T           GL             AE   R  L    KEL 201                                               250
p49      .......KKVM DLSIVRLRFS AFLRASDGSF SLPLKPVTSQ PIHDSKSPGA
p100     .......KKVM DLSIVRLRFS AFLRASDGSF SLPLKPVTSQ PIHDSKSPGA
p105     QAALQQTKEM DLSVVRLMFT AFLPDSTGSF TRRLEPVVSD AIYDSKAPNA
cons.           K M DLS VRL F  AFL  S GSF   L PV S    I DKS P A
```

FIGURE 2A

```
       251                                                          300
p49    SNLKISRMDK TAGSVRGGDE VYLLCDKVQK DDIEVRFYED DENG..WQAF
p100   SNLKISRMDK TAGSVRGGDE VYLLCDKVQK DDIEVRFYED DENG..WQAF
p105   SNLKIVRMDR TAGCVTGGEE IYLLCDKVQK DDIQIRFYEE EENGGVWEGF
cons.  SNLKI RMD  TAG V GG E  YLLCDKVQK DDI  RFYE  ENG  W  F 301                                                          350
p49    GDFSPTDVHK QYAIVFRTPP YHKMKIERPV TVFLQLKRKR GGDVSDSKQF
p100   GDFSPTDVHK QYAIVFRTPP YHKMKIERPV TVFLQLKRKR GGDVSDSKQF
p105   GDFSPTDVHR QFAIVFKTPK YKDINITKPA SVFVQLRRKS DLETSEPKPF
cons.  GDFSPTDVH  Q AIVF TP  Y  I  P    VF QL RK   S   K  F 351                                                          400
p49    TYYPLVEDKE EVQRKRRKAL PTFSQPFGGG SHMGGGSGG. .AAGGYGGA.
p100   TYYPLVEDKE EVQRKRRKAL PTFSQPFGGG SHMGGGSGG. .AAJGYGGA.
p105   LYYPEIKDKE EVQRKRQKLM PNFSDSFGGG SGAGAGGGGM FGSGGGGGT
cons.   YYP  DKE EVQRKR K    P FS  FGGG S  G  G G  G        
p49

401                                                          450
p49    .......... .......... .........GG GE........ ..........
p100   GGGSLGFFPS SLAYSPYQSG AGPMGCYPGG GG........ ..........
p105   GSTGPGYSFP HYGFPTYGGI TFHPGTTKSN AGMKHGTMDT ESKKDPEGCD
cons.  G              Y      G           G
```

FIGURE 2B

```
       451                                                                    500
p49    ..........  .GVLMEGGKV  VREAVEEKNL  GEAGRGLHAC  NP..........
p100   ..........  .GAQMAATVP  SRDSGEEAAE  PSAPSRTPQC  EPQAPEMLQR
p105   KSDDKNTVNL  FGKVIETTEQ  DQEPSEATVG  NGEVTLTYAT  GTKEESAGVQ
cons.              G          T           E          T 501                                                                    550
p49    ..........A  FGRPRQADYL  RSGVQDQ...  .LGQQRETSS  LLKIQTLAGH
p100   AREYNARLFG   LAQRSARALL  DYGVTADARA  LLAGQRH...  LLTAQDENGD
p105   DNLFLEKAMQ   LAKRHANALF  DYAVTGDVKM  LLAVQRH...  LTAVQDENGD
cons.              LA R  A AL  DY VT D     LLA QRH     L  QDENGD 551                                                                    600
p49    GGRRL*.....  ..........  ..........  ..........  ..........
p100   TPLHLAIIHG   QTSVIEQIVY  VIHHAQDLGV  VNLTNHLHQT  PLHLAVITGQ
p105   SVLHLAIIHL   HSQLVRDLLE  VTSGLISDDI  INMRNDLYQT  PLHLAVITKQ
cons.  LHLAIIH                  V           N  N L QT  PLHLAVIT  Q 601                                                                    650
p49    ..........  ..........  ..........  ..........  ..........
p100   TSVVSFLLRV  GADPALLDRH  GDSAMHLALR  AGAGAPELLR  ALLQSGAPAV
p105   EDVVEDLLRA  GADLSLLDRL  GNSVLHLA..  AKEGHDKVLS  ILLKHKKAAL
cons.   VV   LLR   GAD  LLDR   G S  HLA      A  G       L   LL   A
```

FIGURE 2C

```
       651                                                        700
p49    ..........  PQLLHMPDFE  GLYPVHLAVR  ARSPECLDLL  VDSGAEVEAT  ERQGGRTALH
p100   ..........  ..LLDHPNGD  GLNAIHLAMM  SNSLPCLLLL  VAAGADVNAQ  EQKSGRTALH
p105   ..........  ..........  ..........  ..........  ..........  ..........
cons.                 LL  P     GL   HLA     S   CL LL  V  GA V A   E  GRTALH 701                                                        750
p49    LATEMEELGL  VTHLVTKLRA  NVNARTFAGN  TPLHLAAGLG  YPTLTRLLIK  ..........
p100   LAVEHDNISL  AGCLLLEGDA  HVDSTTYDGT  TPLHIAAGRG  STRLAALLKA  ..........
p105   ..........  ..........  ..........  TPLN AAG G   L  LL      ..........
cons.  LA E    L    L       A     V   T G 751                                                        800
p49    AGADIHAENE  EPLCPLPSPP  TSDSDSDSEG  PEKDTRSSFR  GHTPLDLTCS  ..........
p100   AGADPLVENF  EPLYDLDDSW  ENAGEDEGVV  P.........  GTTPLDMATS  ..........
p105   AGAD    EN   EPL  L            P                GTTPLD  TS  ..........
cons.

801                                                        850
p49    TKVKTLLLNA  AQNTMEPPLT  PPSPAGPGLS  LGDTALQNLE  QLLDGPEAQG  ..........
p100   WQVFD.ILNG  KPYEPEFTSD  DLLAQGDMKQ  LAEDVKLQLY  KLLEIPDPDK  ..........
p105   ..........  ..........  ..........  ..........  ..........  ..........
cons.       V  LN             E            G        L      L   P
```

FIGURE 2D

```
       851                                                              900
p49    ..........  SWAELAERLG  LRSLVDTYRQ  ..........  ..........
p100   ..........  ..........  ..........  TTSPSGSLLR  SYELAGGDLA  GLLEALSDMG
p105   NWATLAQKLG  LGILNNAFRL  SPAPSKTLMD  NYEVSGGTVR  ELVEALRQMG
cons.      WA LA   LG L   L         R       PS L          YE GG       L EAL  MG 901                                                              950
p49    ..........  LEEGVRLLRG  PETRDKLPS.  ..........  .TEVKE     DSAYGSQSVE
p100   ..........  ..........  ..........  ..........
p105   YTEAIEVIQA  ASSPVKTTSQ  AHSLPLSPAS  TRQQIDELRD  SDSVCDTGVE
cons.         E          K S                                E                VE 951                                                 989
p49    ..........  QEAEKLGPPP  EPPGGLCHGH  PQPQVH*...  ..........
p100   ..........  ..........  ..........  ..........
p105   TSFRKLSFTE  SLTSGASLLT  LNKMPHDYGQ  EGPLEGKI*
cons.      KL              G              H
```

DNA AND RNA ENCODING PROTEINS USEFUL IN THE REGULATION OF KB-CONTAINING GENES, AND CELLS CONTAINING SAME

This is a division, of application Ser. No. 07/747,781, filed on Aug. 20, 1991, now U.S. Pat. No. 5,324,818.

BACKGROUND OF THE INVENTION

1. Field of the Invention

The present invention relates to genetic sequences and proteins useful in the regulation of genes, particularly in the regulation of κB-containing genes.

2. Discussion of the Background

A twice-repeated 11-base-pair sequence, termed κB, which is known to exist in association with the enhancer of the immunoglobulin κ light chain (Sen et al, *Cell* (1986) 46:705, Sen et al, *Cell* (1986) 47:729) is present in the control elements of numerous genes, including both viral and cellular genes. NF-κB, a regulatory element originally described as a transcription factor that recognizes the κB element of the immunoglobulin (Ig) κ light chain enhancer and which is known to be associated with κ light chain expression, has been found in a variety of viral enhancers, including SV40, CMV, HIV-2 and SIV. κB-related sites have been found in association with several cellular genes, including class I and II MHC genes, IL-2, IL-2 receptor (IL-2Rα), serum amyloid A, β-2 microglobulin, β-interferon, tumor necrosis factor, and T-cell receptor genes.

A κB-like site contributes functionally to IL-2-dependent gene expression and may also regulate IL-2Rα transcription. κB is also found among the regulatory elements upstream of the HIV enhancer. This site was initially identified as a positive regulatory element recognized by DNA binding proteins found to be present in activated, but not resting, T cells. Mutation of the κB sites abolished inducibility of the HIV enhancer in T leukemia cells. A link between the κB site and the tat-I gene was also suggested by the synergistic response of the HIV enhancer to tat-I and NF-κB-mediated stimulation.

Another κB-like site was found upstream of the class I MHC gene. Although this site competes for binding to NF-κB, a DNA binding protein distinct from NF-κB has been identified in MEL and HeLa cells. Baldwin et al, *Proc. Nat. Acad. Sci. (USA)* (1988) 85:723. This protein, termed H2TF1, was detected in nuclear extracts containing no detectable NF-κB binding activity and had a different apparent molecular weight as measured by UV-cross-linking analysis. Another protein, designated KBF1, also recognized this site and may be related in part to NF-κB. Israel et al, *Proc. Nat. Acad. Sci. (USA)* (1987) 84:2653, Yanno et al, *EMBO J* (1987) 6:3317.

Although these proteins recognize κB-like sites, their relationship to the IL-2R κB binding protein(s) and NF-κB is unknown. Similarly, the HIVen86 protein is likely to be distinct from NF-κB since it has a higher apparent molecular weight. Franza et al, *Nature* (1987) 330:391. Its relationship to the IL-2R κB binding protein, which has been designated RκB (NF-rκB), and its role in mediating transactivation dependent on these κB-like sites is also not yet understood. Although the evidence is indirect, it appears that HIVen86 also differs from RκB, which has a higher apparent molecular weight of 100 kD.

While extensive sequence similarity to κB is found among enhancers associated with several genes (Lung et al, *Nature* (1988) 333:776), a second characteristic shared by these sites is their ability to respond to transactivation by the $tax_1$ gene of HTLV-1. At the same time, several lines of evidence suggest differences among κB binding proteins. For example, nuclear extracts from MEL cells display an H2TF1 binding activity in the absence of detectable NF-κB binding. Competition studies showed that both the IL-2RκB and κB sites compete less efficiently than H2TF1 for binding to the site, consistent with previous studies suggesting that a distinct binding protein binds to the H2TF1 site.

Analysis of binding proteins by UV-cross-linking and SDS-page has also revealed multiple radiolabeled complexes, further implicating multiple proteins in κB binding. By UV-cross-linking, several specific complexes have been detected, including proteins of molecular weights of ca. 160, ca. 90, ca. 75, and ca. 50 kD. There is no evidence for differential regulation of these proteins by different NF-κB stimulants since PMA, TNF-α, and IL-1 induce the same set of complexes. The complex of ca. 50 kD is consistent with previous report of NF-κB and/or KBF1. Although a κB binding protein of 86 kD HIVen86A, has also been identified by two-dimensional gel electrophoresis, it is unclear whether the ca. 90 kD protein represents this protein. Both HIVen86 and RκB show no increase in binding following cellular activation. The 160 kD complex has not been previously described.

In summary, at least seven κB binding proteins have been defined to date by either mobility shift analysis, UV-cross-linking, or protein purification. The molecular weight of these proteins range in size from 48 to greater than 300 kD. The various κB binding proteins that have been reported are indicated in Table 1 below, together with their relative specificities for the canonical κB, the class I MHC, and the IL-2RκB sites.

TABLE 1

| Summary of κB Binding Proteins | | | |
|---|---|---|---|
| Name | Specificity | Protein (kD) | CDNA (kb) |
| NF-κB/KBFI | κB = MHC = IL-2RκB | 50 | 4 |
| H2TF-1 | MHC > κB > IL-2RκB | 110 | — |
| EBP-L | MHC = κB | 60 | — |
| HIVen86 | KB = IL-2RκB | 86 | — |
| MBP-1 | MHC > κB > IL-2RκB | ~300 | 9.5 |
| RκB (IL-2RκB) | IL-2RκB > κB > MHC | 95 | 5.5 |

Of these, the cDNAs encoding three of these proteins have been isolated. These cDNAs differ from one another by primary sequence and react with mRNAs of distinct size by northern blot. Taken together, these data indicate that multiple proteins could bind to a set of κB-related sites. Thus, there is a family of κB binding proteins, which, unlike some DNA binding proteins (e.g., c-jun), do not appear to be members of a related multigene family.

The κB sequence is known to exist in association with the regulatory elements of various viral and cellular genes. In light of the obvious interest in regulating gene expression there is accordingly a need for a factor useful in the regulation of κB-containing genes.

SUMMARY OF THE INVENTION

Accordingly, it is an object of this invention to provide novel factors, and materials and methods useful for obtaining and using such factors, useful in the regulation of κB-containing genes.

The above objects, of the invention, and other objects which will become apparent from the description of the invention given hereinbelow, have been surprisingly found to be satisfied by proteins having amino acid sequences related to p49 [SEQ ID NO: 1] and p100 [SEQ ID NO: 2]. More particularly, the inventors have discovered that proteins having amino acid sequences at least 80%, preferably at least 90% and more preferably at least 95%, identical to either (i) the sequence of from amino acid position about 1 to amino acid position about 374 and up to the complete sequence of p49 [SEQ ID NO: 1] or (ii) the sequence of from amino acid position about 1 to amino acid position about 374 and up to amino acid position about 500 of p100 [SEQ ID NO: 2] are useful to stimulate the expression of κB-containing genes. The inventors have also discovered related proteins useful in inhibiting the expression of κB-containing genes. These proteins may be characterized by amino acid sequences at least 80%, preferably at least 90% and more preferably at least 95%, identical to the sequence of from amino acid position about 407 of p100 [SEQ ID NO: 2]. The proteins exhibiting the inhibitory effect may also be characterized by amino acid sequences at least 80%, preferably at least 90% and more preferably at least 95%, identical to the sequence of from either (i) amino acid positions about 1 to about 190 or (ii) positions about 191 to about 374 of p100 [SEQ ID NO: 2] and up to about complete p100 [SEQ ID NO: 2].

BRIEF DESCRIPTION OF THE FIGURES

The figures set forth the deduced amino acid sequence of the p49 [SEQ ID NO: 1] and p100 [SEQ ID NO: 2] NF-κB proteins— two proteins provided by the invention—and their similarity to other NF-κB/rel/dorsal genes. More particularly, FIG. 1 provides a schematic comparison of the major structural features of p49 [SEQ ID NO: 1] and p100 [SEQ ID NO: 2]. FIG. 2 provides the deduced amino acid sequence of p49 [SEQ ID NO: 1] and p100 [SEQ ID NO: 2] and comparison to p105 NF-κB [SEQ ID NO: 3].

DETAILED DESCRIPTION OF THE PREFERRED EMBODIMENTS

Figure 1:
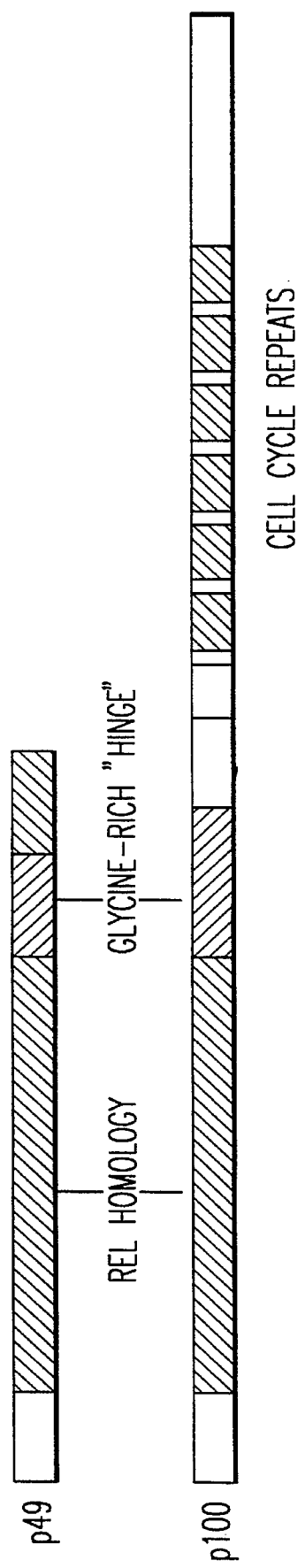

The transcription factor NF-κB is a protein complex which comprises a DNA-binding subunit and an associated transactivation protein (of relative molecular masses 50,000 (50K) and 65K, respectively). Both the 50K and 65K subunits have similarity with the rel oncogene and the Drosophila maternal effect gene dorsal. The 50K DNA-binding subunit was previously thought to be a unique protein, derived from the 105K gene product (p105). The present invention is based on the inventor's discovery of a complementary DNA (cDNA) that encodes an alternative DNA-binding subunit of NF-κB. This cDNA is more similar to p105 NF-κB than other family members and defines a new subset of rel-related genes.

It is synthesized as a ca.100K protein (p100) that is expressed in different cell types, contains cell cycle motifs and, like p105, must be processed to generate a 50K form. A 49K product (p49) can be generated independently from an alternatively spliced transcript; it has specific κB DNA-binding activity and can form heterodimers with other rel proteins. In contrast to the ca.50K protein derived from p105, p49 acts in synergy with p65 to stimulate the human immunodeficiency virus (HIV) enhancer in transiently transfected Jurkat cells. The p49/p100 NF-κB is therefore important in the regulation of κB-containing genes, including HIV.

The present invention accordingly provides proteins useful in the regulation of κB-containing genes. These proteins may be used to either stimulate or inhibit the expression of κB-containing genes. These proteins are based on the inventor's discovery that the amino acid sequence located at positions about 1 to about 374 of p49 [SEQ ID NO: 1] and up to the complete sequence of p49 [SEQ ID NO: 1], simulates the expression of κB-containing genes. (Note that p49 [SEQ ID NO: 1] and p100 [SEQ ID NO: 2] are identical from positions 1 to 374.)

The inventor has further discovered that the amino acid sequence found at about positions about 1 to about 190 of p100 [SEQ ID NO: 2] is a DNA binding domain and that the amino acid sequence found at positions about 191 to about 374 of p100 [SEQ ID NO: 2] is a dimerization interface. And the inventor has still further discovered that the amino acid sequence found at position about 407 of p100 [SEQ ID NO: 2] going all the way to about the carboxyl terminal of the protein is also capable of inhibiting the expression of κB-containing genes.

The proteins provided by the present invention which accordingly act to stimulate κB-containing genes have an amino acid sequence at least 80% identical (i.e. up to 20% of the amino acids have been changed, deleted, or both), preferably 90% identical, and most preferably 95% identical, to the amino acid sequence of amino acid positions about 1 to about 374 of either p49 [SEQ ID NO: 1] or p100 [SEQ ID NO: 2] and optionally up to about the complete sequence of p49 [SEQ ID NO: 1] or up to amino acid position about 500 of p100 [SEQ ID NO: 2].

Proteins useful in inhibiting κB-containing genes provided by the invention are of two related types. The first is a transdominant mutant of p49 [SEQ ID NO: 1] in which either (i) the dimerization interface region of p49 [SEQ ID NO: 1] has been retained (located at positions about 191 to about 374 of p100 [SEQ ID NO: 2]) or (ii) the DNA binding region (located in positions about 1 to about 190 of p100 [SEQ ID NO: 2]) has been retained. In either of these two embodiments the other (i.e. unretained) region has been either removed or altered to cause loss of DNA binding or of dimerization activity, e.g., by removing or replacing at least 10% of its amino acids, preferably at least 25% of its amino acids, to achieve removal of DNA binding or dimerization activity.

This transdominant mutant of p49 [SEQ ID NO: 2] may be a protein having an amino acid sequence at least 80% identical, preferably 90% identical, and most preferably 95% identical, to either (i) the amino acid sequence of amino acid positions about 1 to about 190 or (ii) the amino acid sequence of amino acid positions about 191 to about 374 of either p49 or p100 [SEQ ID NO: 1 or 2] and optionally up to the complete p49 [SEQ ID NO: 1] or complete p100 [SEQ ID NO: 2]. That is, if the protein is one in which the DNA binding region has been altered or removed, the protein may further comprise, attached to its carboxyl end, an amino acid sequence at least 80% identical, preferably 90% identical, and more preferably 95% identical to up to 100%, the amino acid sequence of from positions 374 to the carboxyl end of p100 [SEQ ID NO: 2].

With the above transdominant mutant of p49 [SEQ ID NO: 1] one uses either the protein segment comprising the DNA binding region or the protein segment comprising the dimerization interface region of p49 [SEQ ID NO: 1]. The DNA binding region may be used by itself or it may be used in association with an inactivated dimerization interface, where the inactivation results from removal of at least 10%, or preferably 25% amino acids from the dimerization interface region. If a protein segment corresponding to the dimerization interface region is used, it may be used by itself or in association with an inactivated DNA binding region, where inactivation is caused by the removal of at least 10%, preferably at least 25% of the amino acids from the DNA binding region.

Another group of κB inhibiting proteins provided by the present invention have an amino acid sequence at least 80% identical, preferably 90% identical, and most preferably 95% identical to the sequence of amino acid at positions about 407 of p100 [SEQ ID NO: 2] to about the carboxy end of p100 [SEQ ID NO: 2].

The present invention also provides DNA and RNA sequences encoding to the above proteins, corresponding antisense RNA sequences, vectors useful to express these proteins, and both eukaryotic and prokaryotic cells containing these DNA and/or RNA sequences, further optionally containing a κB-containing gene.

The antisense RNA sequences provided by the present invention may be one of five different types. The first is an antisense RNA sequence which is at least 20 nucleotides-long and corresponds to an amino acid sequence falling within positions 1 to 374 of p49 [SEQ ID NO: 1], inclusive. The second is an antisense RNA sequence which is at least 20 nucleotides-long and corresponds to an amino acid sequence falling within the sequence of p49 [SEQ ID NO: 1]. The third is an antisense RNA sequence which is at least 20 nucleotides-long and corresponds to an amino acid sequence falling within the sequence of p100 [SEQ ID NO: 2]. The fourth is an antisense RNA sequence which is at least 20 nucleotides-long which corresponds to an amino acid sequence falling within the sequence of from position 375 to the carboxyl end of p49 [SEQ ID NO: 1], inclusive. The fifth is an antisense RNA sequence which is at least 20 nucleotides-long and corresponds to an amino acid sequence falling within positions 375 to the carboxyl end of p100 [SEQ ID NO: 2], inclusive.

These antisense RNA sequences may be used in accordance with known techniques (see, e.g., Zamecnik et al., Proc. Nat. Acad. Sci. (USA), (1986) 83:4143–4146) to inhibit or block cellular expression of the genes encoding either p49 [SEQ ID NO: 1] or p100 [SEQ ID NO: 2]. More particularly the above first, second and third antisense RNA sequences may be used to inhibit or block expression of either p49 [SEQ ID NO: 1] or p100 [SEQ ID NO: 2]. The fourth antisense RNA sequence may be used to inhibit or block expression of p49 [SEQ ID NO: 1] because it is drawn to a sequence unique to p49 [SEQ ID NO: 1]. The above fifth antisense RNA sequence may be used to inhibit or block expression of p100 [SEQ ID NO: 2] because it is drawn to a sequence unique to p100 [SEQ ID NO: 2].

The eukaryotic and prokaryotic cells provided by the present invention contain the DNA and/or RNA sequences encoding a present protein, optionally together with a κB-containing gene. These latter sequences (i.e., the sequences containing the κB sites) are present in these cells in a geometry permitting regulation of the κB-containing gene by the proteins of the present invention.

The p49/p100 subunit of NF-κB provided by the invention can be used to regulate the expression of recombinant genes in eukaryotic or prokaryotic cells. In one form of this method, the p49/p100 gene can be overexpressed in a host cell which contains a separate κB-dependent enhancer to express a given recombinant gene. When the p49 gene is overexpressed, the κB-regulated enhancer will stimulate expression of the recombinant gene of interest.

In another method, it is possible to use the κB site to block transcriptional activation. By placing the κB binding sites within a promoter near the transcriptional initiation site, it would interfere with transcriptional initiation or elongation when the recombinant p49/p100 proteins could bind to these sites. It is therefore possible to inhibit expression of a specific recombinant gene when this molecule is overexpressed.

Another way to regulate expression of recombinant genes within cells is to make a fusion protein between p49 (or p100) gene products, for example, the DNA binding and dimerization domains and fuse them to an acidic transactivation domain, such as that of the herpesvirus transactivator, VP16. Such chimeric constructs would provide a high level of constitutive transactivation to κB-dependent plasmids.

Several such plasmids can be synthesized whereby fusion proteins have been linked to the 3'-end of either p49 or an equivalent of p100, creating potent transactivators. Such chimeric transactivators can also be used to overexpress recombinant proteins with cells.

The NF-κB-related DNA and RNA or protein sequences provided by the inventors can be utilized for a variety of different functions. First, the recombinant protein can be used to generate antibodies against this gene product to detect this protein within cells or tissues. Since these proteins are involved in the regulation of HIV and may also be related to cell division and malignancy, this would provide a useful assay to determine the degree of progression of HIV or the degree of activation of malignant cells.

In addition, the DNA or RNA sequences can be measured directly following HIV infection as an indicator of the activity of virus within cells. In recent studies, the inventors have noted a decrease in p100 expression following HIV infection in cell culture. The recombinant proteins can also be used to generate transdominant mutants which can be used to inhibit activation of HIV, normal cellular genes, or cell replication. The purified recombinant proteins may also be used to define mechanisms of transcriptional activation in the laboratory to determine the specificity of DNA binding, and to determine the 3-dimensional structure of these proteins for further attempts at molecular modeling and rational drug design.

Cultures of *E. coli* XL-blue cells transformed with bluescript plasmids containing p49 [SEQ ID NO: 1] or p100 [SEQ ID NO: 2] encoding inserts have been deposited on Aug. 20, 1991 in the permanent culture collection of the American Type Culture Collection (ATCC), located at 12301 Parklawn Drive, Rockville, Md. 20852 USA. These cultures have been accorded the following accession numbers: ATCC68673 and ATCC68672.

Having generally described this invention, a further understanding can be obtained by reference to certain specific examples which are provided herein for purposes of illustration only and are not intended to be limiting unless otherwise specified.

EXPERIMENTAL

To characterize the molecular structure of NF-κB and its mechanism of activation, the inventor attempted to identify cDNAs that encode proteins within this complex. Trypsin digested κB binding proteins purified from bovine spleen were sequenced. Three peptides so obtained were identical to a DNA binding subunit of human NF-κB/KBF1, while another was 75% identical to a homologous peptide of p105. This peptide sequence suggested the existence of an alternative NF-κB protein. A PCR probe amplified from degenerate primers was found to be identical to a 700 bp fragment of human c-rel and was used for low stringency hybridization.

From $6 \times 10^5$ recombinants, two clones were identified which hybridized at low stringency. By Southern blot analysis at high stringency, this gene was present in single copy, and Northern blot analysis revealed at least two hybridizable RNA species of ~1.9 kb and ~3.5 kb, demonstrating that multiple species of p49 existed, and their relative abundance varied among different cell types. For example, the larger 3.5 kb species, found in all cells examined, was the predominant form in YT T leukemia cells; but both transcripts were present equally in the JY B cell line.

To characterize the larger mRNA species, additional cDNA clones were isolated and sequenced. The clone for the shorter transcript contained a 1341 bp open reading frame, predicting a protein of MW ~49,100. The longer clone encoded a protein of predicted MW, ~100,634 kd. These sequences were identical through amino acid 374, into the glycine-rich putative hinge region, after which they diverged. The amino acid sequence in the common N-terminal region was similar (26% identity) to NF-κB, dorsal and rel, with greatest similarity between p49/p100 and p105 (60% identity). One subregion contained conserved cysteine and histidine residues that do not form a classic zinc finger structure. Interestingly, κB-binding activity is dependent upon zinc, and, analogous to the tat-I gene of HIV, may form an alternative structure which participates in dimerization or nucleic acid binding. The longer transcript contained repeated sequences in the C-terminal region with homology to motifs in p105 and cell cycle genes. Among these family members, p100 NF-κB is most closely related to p105 NF-κB (41% identity), while p65 is most similar to c-rel (50% identity).

To characterize the DNA binding activity of the p49 cDNA, the electrophoretic mobility shift assay (EMSA) was performed using a prokaryotic expression system. The predominant product of ~49 kd displayed specific κB binding activity which was competed by the H-2 and HIV κB sites, but not by a single base pair mutant of HIV or an unrelated IL-2 octamer site. Interaction of p49 with other rel family members was examined by immunoprecipitation in a wheat germ co-translation system similar to p105(Xba I), p49 associated with c-rel.

To determine whether p49 interacts with other NF-κB/rel proteins to stimulate transcription, eukaryotic expression vectors were transfected into Jurkat cells. Transfection of p49 alone stimulated κB enhancer activity slightly, while p65 at higher concentrations significantly increased κB-dependent transcription. Transfection of low amounts ($\leq 1$ μg) of either p49 or p65 caused minimal stimulation, but when co-transfected together, they acted in synergy to stimulate a κB reporter plasmid. This stimulation was more effective than the combination of "p50" [p105(Rsa I)] and p65, suggesting that p49 was more effective in cooperating with p65. When analyzed with the HIV-CAT reporter, the p49/p65 combination, but not p50 [p105(Rsa I)]/p65, stimulated HIV-CAT activity, and the effect required an intact κB regulatory element. A truncated p100 (48.5 kd form) showed similar stimulation, in contrast to full-length p100 which was inactive, suggesting that differences in the rel-conserved domain mediate this effect.

These findings demonstrate that κB-dependent transcription is regulated by the p49/100 gene products. p65 and rel are putative transcriptional activation subunits with intrinsic DNA binding activity which associate with another DNA binding subunit, previously thought to be a single gene product derived from p105. These findings suggest that p49/100 represents an alternative DNA binding subunit of NF-κB which synergizes effectively with p65 to activate κB-dependent transcription. Many proteins can bind to κB-related sites, some of which are not NF-κB/rel-related. Although a variety of κB-binding proteins have been defined biochemically, their identification has remained equivocal since related antigenic epitopes are contained in their amino terminal region. As with p49/100, the identification of these cDNAs allows more definitive analysis of their expression and function. The interaction of p49/100 with other proteins and its potential alternative modes of regulation may provide additional mechanisms to regulate the transcription of HIV and different κB-containing genes.

Obviously, numerous modifications and variations of the present invention are possible in light of the above teachings. It is therefore to be understood that within the scope of the appended claims, the invention may be practiced otherwise than as specifically described herein.

---

What is claimed as new and desired to be secured by Letters Patent of the United States is:

1. An isolated DNA sequence which encodes the protein of the sequence shown in SEQ ID NO.:1.
2. An isolated RNA sequence which encodes the protein of the sequence shown in SEQ ID NO.:1.
3. A cell transformed with the isolated DNA sequence of claim 1.
4. An isolated DNA sequence which encodes the protein of the sequence shown in SEQ ID NO.:2.
5. An isolated RNA sequence which encodes the protein of the sequence shown in SEQ ID NO.:2.
6. A cell transformed with the isolated DNA sequence of claim 4.
7. An isolated antisense RNA sequence which is fully complementary to the RNA sequence of claim 2 or 5.
8. The DNA sequence of claim 1 further comprising a κB-containing gene.
9. A cell comprising a κB-containing gene and the DNA sequence of claim 1, wherein said DNA sequence is capable of stimulating the expression of said κB-containing gene.
10. The cell of claim 9, wherein said cell is a prokaryotic cell.
11. The cell of claim 9, wherein said cell is a eukaryotic cell.
12. The isolated DNA sequence of claim 4 further comprising a κB-containing gene.
13. A cell comprising a κB-containing gene and the isolated DNA sequence of claim 4, wherein said DNA sequence is capable of stimulating the expression of said κB-containing gene.

\* \* \* \* \*

UNITED STATES PATENT AND TRADEMARK OFFICE
CERTIFICATE OF CORRECTION

PATENT NO. : 5,460,965
DATED : October 24, 1995
INVENTOR(S) : Gary J. Nabel et al It is certified that error appears in the above-indentified patent and that said Letters Patent is hereby corrected as shown below:

Column 2, Table 1, Line 43, "EBP-L" should read --"EBP-1--.

Signed and Sealed this

Thirteenth Day of August, 1996

Attest:

BRUCE LEHMAN

Attesting Officer      Commissioner of Patents and Trademarks

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 447 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:1:

```
Met  Glu  Ser  Cys  Tyr  Asn  Pro  Gly  Leu  Asp  Gly  Ile  Ile  Glu  Tyr  Asp
 1                 5                           10                          15

Asp  Phe  Lys  Leu  Asn  Ser  Ser  Ile  Val  Glu  Pro  Lys  Glu  Pro  Ala  Pro
             20                          25                          30
```

```
Glu  Thr  Ala  Asp  Gly  Pro  Tyr  Leu  Val  Ile  Val  Glu  Gln  Pro  Lys  Gln
          35                  40                    45

Arg  Gly  Phe  Arg  Phe  Arg  Tyr  Gly  Cys  Glu  Gly  Pro  Ser  His  Gly  Gly
     50                       55                    60

Leu  Pro  Gly  Ala  Ser  Ser  Glu  Lys  Gly  Arg  Lys  Thr  Tyr  Pro  Thr  Val
65                       70                    75                         80

Lys  Ile  Cys  Asn  Tyr  Glu  Gly  Pro  Ala  Lys  Ile  Glu  Val  Asp  Leu  Val
                    85                       90                          95

Thr  His  Ser  Asp  Pro  Pro  Arg  Ala  His  Ala  His  Ser  Leu  Val  Gly  Lys
               100                      105                    110

Gln  Cys  Ser  Glu  Leu  Gly  Ile  Cys  Ala  Val  Ser  Val  Gly  Pro  Lys  Asp
               115                      120                    125

Met  Thr  Ala  Gln  Phe  Asn  Asn  Leu  Gly  Val  Leu  His  Val  Thr  Lys  Lys
          130                      135                    140

Asn  Met  Met  Gly  Thr  Met  Ile  Gln  Lys  Leu  Gln  Arg  Gln  Arg  Leu  Arg
145                      150                    155                         160

Ser  Arg  Pro  Gln  Gly  Leu  Thr  Glu  Ala  Glu  Gln  Arg  Glu  Leu  Glu  Gln
                    165                      170                    175

Glu  Ala  Lys  Glu  Leu  Lys  Lys  Val  Met  Asp  Leu  Ser  Ile  Val  Arg  Leu
               180                      185                    190

Arg  Phe  Ser  Ala  Phe  Leu  Arg  Ala  Ser  Asp  Gly  Ser  Phe  Ser  Leu  Pro
               195                      200                    205

Leu  Lys  Pro  Val  Thr  Ser  Gln  Pro  Ile  His  Asp  Ser  Lys  Ser  Pro  Gly
210                      215                      220

Ala  Ser  Asn  Leu  Lys  Ile  Ser  Arg  Met  Asp  Lys  Thr  Ala  Gly  Ser  Val
225                      230                      235                         240

Arg  Gly  Gly  Asp  Glu  Val  Tyr  Leu  Leu  Cys  Asp  Lys  Val  Gln  Lys  Asp
               245                      250                         255

Asp  Ile  Glu  Val  Arg  Phe  Tyr  Glu  Asp  Glu  Asn  Gly  Trp  Gln  Ala
               260                      265                    270

Phe  Gly  Asp  Phe  Ser  Pro  Thr  Asp  Val  His  Lys  Gln  Tyr  Ala  Ile  Val
               275                      280                    285

Phe  Arg  Thr  Pro  Pro  Tyr  His  Lys  Met  Lys  Ile  Glu  Arg  Pro  Val  Thr
     290                      295                    300

Val  Phe  Leu  Gln  Leu  Lys  Arg  Lys  Arg  Gly  Gly  Asp  Val  Ser  Asp  Ser
305                      310                    315                         320

Lys  Gln  Phe  Thr  Tyr  Tyr  Pro  Leu  Val  Glu  Asp  Lys  Glu  Glu  Val  Gln
                    325                      330                    335

Arg  Lys  Arg  Arg  Lys  Ala  Leu  Pro  Thr  Phe  Ser  Gln  Pro  Phe  Gly  Gly
               340                      345                    350

Gly  Ser  His  Met  Gly  Gly  Gly  Ser  Gly  Gly  Ala  Ala  Gly  Gly  Tyr  Gly
          355                      360                    365

Gly  Ala  Gly  Gly  Gly  Glu  Gly  Val  Leu  Met  Glu  Gly  Gly  Val  Lys  Val
     370                      375                    380

Arg  Glu  Ala  Val  Glu  Glu  Lys  Asn  Leu  Gly  Glu  Ala  Gly  Arg  Gly  Leu
385                      390                    395                         400

His  Ala  Cys  Asn  Pro  Ala  Phe  Gly  Arg  Pro  Arg  Gln  Ala  Asp  Tyr  Leu
                    405                      410                         415

Arg  Ser  Gly  Val  Gln  Asp  Gln  Leu  Gly  Gln  Gln  Arg  Glu  Thr  Ser  Ser
               420                      425                    430

Leu  Leu  Lys  Ile  Gln  Thr  Leu  Ala  Gly  His  Gly  Gly  Arg  Arg  Leu
               435                      440                    445
```

( 2 ) INFORMATION FOR SEQ ID NO:2:

( i ) SEQUENCE CHARACTERISTICS:
        ( A ) LENGTH: 899 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:2:

```
Met Glu Ser Cys Tyr Asn Pro Gly Leu Asp Gly Ile Ile Glu Tyr Asp
 1               5                  10                  15
Asp Phe Lys Leu Asn Ser Ser Ile Val Glu Pro Lys Glu Pro Ala Pro
            20                  25                  30
Glu Thr Ala Asp Gly Pro Tyr Leu Val Ile Val Glu Gln Pro Lys Gln
        35                  40                  45
Arg Gly Phe Arg Phe Arg Tyr Gly Cys Glu Gly Pro Ser His Gly Gly
    50                  55                  60
Leu Pro Gly Ala Ser Ser Glu Lys Gly Arg Lys Thr Tyr Pro Thr Val
65                  70                  75                  80
Lys Ile Cys Asn Tyr Glu Gly Pro Ala Lys Ile Glu Val Asp Leu Val
                85                  90                  95
Thr His Ser Asp Pro Pro Arg Ala His Ala His Ser Leu Val Gly Lys
            100                 105                 110
Gln Cys Ser Glu Leu Gly Ile Cys Ala Val Ser Val Gly Pro Lys Asp
        115                 120                 125
Met Thr Ala Gln Phe Asn Asn Leu Gly Val Leu His Val Thr Lys Lys
    130                 135                 140
Asn Met Met Gly Thr Met Ile Gln Lys Leu Gln Arg Gln Arg Leu Arg
145                 150                 155                 160
Ser Arg Pro Gln Gly Leu Thr Glu Ala Glu Gln Arg Glu Leu Glu Gln
                165                 170                 175
Glu Ala Lys Glu Leu Lys Lys Val Met Asp Leu Ser Ile Val Arg Leu
            180                 185                 190
Arg Phe Ser Ala Phe Leu Arg Ala Ser Asp Gly Ser Phe Ser Leu Pro
        195                 200                 205
Leu Lys Pro Val Thr Ser Gln Pro Ile His Asp Ser Lys Ser Pro Gly
    210                 215                 220
Ala Ser Asn Leu Lys Ile Ser Arg Met Asp Lys Thr Ala Gly Ser Val
225                 230                 235                 240
Arg Gly Gly Asp Glu Val Tyr Leu Leu Cys Asp Lys Val Gln Lys Asp
                245                 250                 255
Asp Ile Glu Val Arg Phe Tyr Glu Asp Asp Glu Asn Gly Trp Gln Ala
            260                 265                 270
Phe Gly Asp Phe Ser Pro Thr Asp Val His Lys Gln Tyr Ala Ile Val
        275                 280                 285
Phe Arg Thr Pro Pro Tyr His Lys Met Lys Ile Glu Arg Pro Val Thr
    290                 295                 300
Val Phe Leu Gln Leu Lys Arg Lys Arg Gly Gly Asp Val Ser Asp Ser
305                 310                 315                 320
Lys Gln Phe Thr Tyr Tyr Pro Leu Val Glu Asp Lys Glu Glu Val Gln
                325                 330                 335
Arg Lys Arg Arg Lys Ala Leu Pro Thr Phe Ser Gln Pro Phe Gly Gly
            340                 345                 350
Gly Ser His Met Gly Gly Gly Ser Gly Gly Ala Ala Gly Gly Tyr Gly
        355                 360                 365
```

| | | | | | | | | | | | | | | |
|---|---|---|---|---|---|---|---|---|---|---|---|---|---|---|
|Gly|Ala|Gly|Gly|Gly|Gly|Ser|Leu|Gly|Phe|Phe|Pro|Ser|Ser|Leu|Ala|
| |370| | | | |375| | | |380| | | | |
|Tyr|Ser|Pro|Tyr|Gln|Ser|Gly|Ala|Gly|Pro|Met|Gly|Cys|Tyr|Pro|Gly|
|385| | | |390| | | | |395| | | | | |400|
|Gly|Gly|Gly|Gly|Ala|Gln|Met|Ala|Ala|Thr|Val|Pro|Ser|Arg|Asp|Ser|
| | | | |405| | | |410| | | | |415| |
|Gly|Glu|Glu|Ala|Ala|Glu|Pro|Ser|Ala|Pro|Ser|Arg|Thr|Pro|Gln|Cys|
| | | |420| | | |425| | | | |430| | |
|Glu|Pro|Gln|Ala|Pro|Glu|Met|Leu|Gln|Arg|Ala|Arg|Glu|Tyr|Asn|Ala|
| | |435| | | |440| | | |445| | | | |
|Arg|Leu|Phe|Gly|Leu|Ala|Gln|Arg|Ser|Ala|Arg|Ala|Leu|Leu|Asp|Tyr|
| |450| | | |455| | | | |460| | | | |
|Gly|Val|Thr|Ala|Asp|Ala|Arg|Ala|Leu|Leu|Ala|Gly|Gln|Arg|His|Leu|
|465| | | |470| | | | |475| | | | | |480|
|Leu|Thr|Ala|Gln|Asp|Glu|Asn|Gly|Asp|Thr|Pro|Leu|His|Leu|Ala|Ile|
| | | |485| | | |490| | | | |495| | |
|Ile|His|Gly|Gln|Thr|Ser|Val|Ile|Glu|Gln|Ile|Val|Tyr|Val|Ile|His|
| | | |500| | | |505| | | | |510| | |
|His|Ala|Gln|Asp|Leu|Gly|Val|Val|Asn|Leu|Thr|Asn|His|Leu|His|Gln|
| | |515| | | |520| | | | |525| | | |
|Thr|Pro|Leu|His|Leu|Ala|Val|Ile|Thr|Gly|Gln|Thr|Ser|Val|Val|Ser|
| |530| | | |535| | | | |540| | | | |
|Phe|Leu|Leu|Arg|Val|Gly|Ala|Asp|Pro|Ala|Leu|Leu|Asp|Arg|His|Gly|
|545| | | |550| | | | |555| | | | | |560|
|Asp|Ser|Ala|Met|His|Leu|Ala|Leu|Arg|Ala|Gly|Ala|Gly|Ala|Pro|Glu|
| | | |565| | | |570| | | | |575| | |
|Leu|Leu|Arg|Ala|Leu|Leu|Gln|Ser|Gly|Ala|Pro|Ala|Val|Pro|Gln|Leu|
| | |580| | | |585| | | | |590| | | |
|Leu|His|Met|Pro|Asp|Phe|Glu|Gly|Leu|Tyr|Pro|Val|His|Leu|Ala|Val|
| |595| | | |600| | | | |605| | | | |
|Arg|Ala|Arg|Ser|Pro|Glu|Cys|Leu|Asp|Leu|Leu|Val|Asp|Ser|Gly|Ala|
|610| | | |615| | | | |620| | | | | | |
|Glu|Val|Glu|Ala|Thr|Glu|Arg|Gln|Gly|Gly|Arg|Thr|Ala|Leu|His|Leu|
|625| | | |630| | | | |635| | | | | |640|
|Ala|Thr|Glu|Met|Glu|Glu|Leu|Gly|Leu|Val|Thr|His|Leu|Val|Thr|Lys|
| | | |645| | | |650| | | | |655| | |
|Leu|Arg|Ala|Asn|Val|Asn|Ala|Arg|Thr|Phe|Ala|Gly|Asn|Thr|Pro|Leu|
| | |660| | | |665| | | | |670| | | |
|His|Leu|Ala|Ala|Gly|Leu|Gly|Tyr|Pro|Thr|Leu|Thr|Arg|Leu|Leu|Leu|
| |675| | | |680| | | | |685| | | | |
|Lys|Ala|Gly|Ala|Asp|Ile|His|Ala|Glu|Asn|Glu|Glu|Pro|Leu|Cys|Pro|
| |690| | | |695| | | | |700| | | | |
|Leu|Pro|Ser|Pro|Pro|Thr|Ser|Asp|Ser|Asp|Ser|Asp|Ser|Glu|Gly|Pro|
|705| | | |710| | | |715| | | | | | |720|
|Glu|Lys|Asp|Thr|Arg|Ser|Ser|Phe|Arg|Gly|His|Thr|Pro|Leu|Asp|Leu|
| | | |725| | | |730| | | | |735| | |
|Thr|Cys|Ser|Thr|Lys|Val|Lys|Thr|Leu|Leu|Asn|Ala|Ala|Gln|Asn|
| | |740| | | |745| | | | |750| | | |
|Thr|Met|Glu|Pro|Pro|Leu|Thr|Pro|Pro|Ser|Pro|Ala|Gly|Pro|Gly|Leu|
| |755| | | |760| | | | |765| | | | |
|Ser|Leu|Gly|Asp|Thr|Ala|Leu|Gln|Asn|Leu|Glu|Gln|Leu|Leu|Asp|Gly|
| |770| | | |775| | | | |780| | | | |
|Pro|Glu|Ala|Gln|Gly|Ser|Trp|Ala|Glu|Leu|Ala|Glu|Arg|Leu|Gly|Leu|
|785| | | |790| | | | |795| | | | | |800|

5,460,965
15                                    16
                      -continued Arg  Ser  Leu  Val  Asp  Thr  Tyr  Arg  Gln  Thr  Thr  Ser  Pro  Ser  Gly  Ser
                    805                 810                      815

Leu  Leu  Arg  Ser  Tyr  Glu  Leu  Ala  Gly  Gly  Asp  Leu  Ala  Gly  Leu  Leu
               820                      825                      830

Glu  Ala  Leu  Ser  Asp  Met  Gly  Leu  Glu  Glu  Gly  Val  Arg  Leu  Leu  Arg
          835                 840                      845

Gly  Pro  Glu  Thr  Arg  Asp  Lys  Leu  Pro  Ser  Thr  Glu  Val  Lys  Glu  Asp
     850                           855                 860

Ser  Ala  Tyr  Gly  Ser  Gln  Ser  Val  Glu  Gln  Glu  Ala  Glu  Lys  Leu  Gly
865                      870                      875                      880

Pro  Pro  Pro  Glu  Pro  Pro  Gly  Gly  Leu  Cys  His  Gly  His  Pro  Gln  Pro
               885                      890                      895

Gln  Val  His (2) INFORMATION FOR SEQ ID NO:3:

(i) SEQUENCE CHARACTERISTICS:
      (A) LENGTH: 969 amino acids
      (B) TYPE: amino acid
      (D) TOPOLOGY: unknown (ii) MOLECULE TYPE: protein (xi) SEQUENCE DESCRIPTION: SEQ ID NO:3:

Met  Ala  Glu  Asp  Asp  Pro  Tyr  Leu  Gly  Arg  Pro  Glu  Gln  Met  Phe  His
1                   5                   10                      15

Leu  Asp  Pro  Ser  Leu  Thr  His  Thr  Ile  Phe  Asn  Pro  Glu  Val  Phe  Gln
               20                  25                      30

Pro  Gln  Met  Ala  Leu  Pro  Thr  Ala  Asp  Gly  Pro  Tyr  Leu  Gln  Ile  Leu
          35                 40                      45

Glu  Gln  Pro  Lys  Gln  Arg  Gly  Phe  Arg  Phe  Arg  Tyr  Val  Cys  Glu  Gly
     50                      55                      60

Pro  Ser  His  Gly  Gly  Leu  Pro  Gly  Ala  Ser  Ser  Glu  Lys  Asn  Lys  Lys
65                       70                      75                       80

Ser  Tyr  Pro  Gln  Val  Lys  Ile  Cys  Asn  Tyr  Val  Gly  Pro  Ala  Lys  Val
                    85                  90                       95

Ile  Val  Gln  Leu  Val  Thr  Asn  Gly  Lys  Asn  Ile  His  Leu  His  Ala  His
               100                 105                     110

Ser  Leu  Val  Gly  Lys  His  Cys  Glu  Asp  Gly  Ile  Cys  Thr  Val  Thr  Ala
          115                 120                     125

Gly  Pro  Lys  Asp  Met  Val  Val  Gly  Phe  Ala  Asn  Leu  Gly  Ile  Leu  His
     130                      135                     140

Val  Thr  Lys  Lys  Lys  Val  Phe  Glu  Thr  Leu  Glu  Ala  Arg  Met  Thr  Glu
145                       150                 155                      160

Ala  Cys  Ile  Arg  Gly  Tyr  Asn  Pro  Gly  Leu  Leu  Val  His  Pro  Asp  Leu
                    165                 170                      175

Ala  Tyr  Leu  Gln  Ala  Glu  Gly  Gly  Gly  Asp  Arg  Gln  Leu  Gly  Asp  Arg
               180                     185                      190

Glu  Lys  Glu  Leu  Ile  Arg  Gln  Ala  Ala  Leu  Gln  Gln  Thr  Lys  Glu  Met
          195                      200                      205

Asp  Leu  Ser  Val  Val  Arg  Leu  Met  Phe  Thr  Ala  Phe  Leu  Pro  Asp  Ser
     210                      215                      220

Thr  Gly  Ser  Phe  Thr  Arg  Arg  Leu  Glu  Pro  Val  Val  Ser  Asp  Ala  Ile
225                      230                      235                      240

Tyr  Asp  Ser  Lys  Ala  Pro  Asn  Ala  Ser  Asn  Leu  Lys  Ile  Val  Arg  Met
                    245                 250                      255

```
Asp  Arg  Thr  Ala  Gly  Cys  Val  Thr  Gly  Gly  Glu  Glu  Ile  Tyr  Leu  Leu
               260                 265                      270

Cys  Asp  Lys  Val  Gln  Lys  Asp  Asp  Ile  Gln  Ile  Arg  Phe  Tyr  Glu  Glu
          275                      280                      285

Glu  Glu  Asn  Gly  Gly  Val  Trp  Glu  Gly  Phe  Gly  Asp  Phe  Ser  Pro  Thr
     290                      295                      300

Asp  Val  His  Arg  Gln  Phe  Ala  Ile  Val  Phe  Lys  Thr  Pro  Lys  Tyr  Lys
305                      310                 315                           320

Asp  Ile  Asn  Ile  Thr  Lys  Pro  Ala  Ser  Val  Phe  Val  Gln  Leu  Arg  Arg
                    325                      330                      335

Lys  Ser  Asp  Leu  Glu  Thr  Ser  Glu  Pro  Lys  Pro  Phe  Leu  Tyr  Tyr  Pro
               340                      345                      350

Glu  Ile  Lys  Asp  Lys  Glu  Glu  Val  Gln  Arg  Lys  Arg  Gln  Lys  Leu  Met
               355                 360                      365

Pro  Asn  Phe  Ser  Asp  Ser  Phe  Gly  Gly  Gly  Ser  Gly  Ala  Gly  Ala  Gly
     370                      375                      380

Gly  Gly  Gly  Met  Phe  Gly  Ser  Gly  Gly  Gly  Gly  Gly  Thr  Gly  Ser
385                      390                      395                      400

Thr  Gly  Pro  Gly  Tyr  Ser  Phe  Pro  His  Tyr  Gly  Phe  Pro  Thr  Tyr  Gly
               405                      410                      415

Gly  Ile  Thr  Phe  His  Pro  Gly  Thr  Thr  Lys  Ser  Asn  Ala  Gly  Met  Lys
               420                      425                      430

His  Gly  Thr  Met  Asp  Thr  Glu  Ser  Lys  Lys  Asp  Pro  Glu  Gly  Cys  Asp
               435                      440                      445

Lys  Ser  Asp  Asp  Lys  Asn  Thr  Val  Asn  Leu  Phe  Gly  Lys  Val  Ile  Glu
450                      455                      460

Thr  Thr  Glu  Gln  Asp  Gln  Glu  Pro  Ser  Glu  Ala  Thr  Val  Gly  Asn  Gly
465                      470                      475                      480

Glu  Val  Thr  Leu  Thr  Tyr  Ala  Thr  Gly  Thr  Lys  Glu  Glu  Ser  Ala  Gly
               485                      490                      495

Val  Gln  Asp  Asn  Leu  Phe  Leu  Glu  Lys  Ala  Met  Gln  Leu  Ala  Lys  Arg
               500                      505                      510

His  Ala  Asn  Ala  Leu  Phe  Asp  Tyr  Ala  Val  Thr  Gly  Asp  Val  Lys  Met
               515                      520                      525

Leu  Leu  Ala  Val  Gln  Arg  His  Leu  Thr  Ala  Val  Gln  Asp  Glu  Asn  Gly
     530                      535                      540

Asp  Ser  Val  Leu  His  Leu  Ala  Ile  Ile  His  Leu  His  Ser  Gln  Leu  Val
545                      550                      555                      560

Arg  Asp  Leu  Leu  Glu  Val  Thr  Ser  Gly  Leu  Ile  Ser  Asp  Asp  Ile  Ile
               565                      570                      575

Asn  Met  Arg  Asn  Asp  Leu  Tyr  Gln  Thr  Pro  Leu  His  Leu  Ala  Val  Ile
               580                      585                      590

Thr  Lys  Gln  Glu  Asp  Val  Val  Glu  Asp  Leu  Leu  Arg  Ala  Gly  Ala  Asp
          595                      600                      605

Leu  Ser  Leu  Leu  Asp  Arg  Leu  Gly  Asn  Ser  Val  Leu  His  Leu  Ala  Ala
     610                      615                      620

Lys  Glu  Gly  His  Asp  Lys  Val  Leu  Ser  Ile  Leu  Leu  Lys  His  Lys  Lys
625                      630                      635                      640

Ala  Ala  Leu  Leu  Leu  Asp  His  Pro  Asn  Gly  Asp  Gly  Leu  Asn  Ala  Ile
               645                      650                      655

His  Leu  Ala  Met  Met  Ser  Asn  Ser  Leu  Pro  Cys  Leu  Leu  Leu  Leu  Val
               660                      665                      670

Ala  Ala  Gly  Ala  Asp  Val  Asn  Ala  Gln  Glu  Gln  Lys  Ser  Gly  Arg  Thr
```

|     | 675 |     |     |     |     | 680 |     |     |     |     | 685 |     |     |     |
|-----|-----|-----|-----|-----|-----|-----|-----|-----|-----|-----|-----|-----|-----|-----|
| Ala | Leu 690 | His | Leu | Ala | Val | Glu 695 | His | Asp | Asn | Ile | Ser 700 | Leu | Ala | Gly | Cys |
| Leu 705 | Leu | Leu | Glu | Gly | Asp 710 | Ala | His | Val | Asp | Ser 715 | Thr | Thr | Tyr | Asp | Gly 720 |
| Thr | Thr | Pro | Leu | His 725 | Ile | Ala | Ala | Gly | Arg 730 | Gly | Ser | Thr | Arg | Leu 735 | Ala |
| Ala | Leu | Leu | Lys 740 | Ala | Ala | Gly | Ala | Asp 745 | Pro | Leu | Val | Glu | Asn 750 | Phe | Glu |
| Pro | Leu | Tyr 755 | Asp | Leu | Asp | Asp | Ser 760 | Trp | Glu | Asn | Ala | Gly 765 | Glu | Asp | Glu |
| Gly | Val 770 | Val | Pro | Gly | Thr | Thr 775 | Pro | Leu | Asp | Met | Ala 780 | Thr | Ser | Trp | Gln |
| Val 785 | Phe | Asp | Ile | Leu | Asn 790 | Gly | Lys | Pro | Tyr | Glu 795 | Pro | Glu | Phe | Thr | Ser 800 |
| Asp | Asp | Leu | Leu | Ala 805 | Gln | Gly | Asp | Met | Lys 810 | Gln | Leu | Ala | Glu | Asp 815 | Val |
| Lys | Leu | Gln | Leu 820 | Tyr | Lys | Leu | Leu | Glu 825 | Ile | Pro | Asp | Pro | Asp 830 | Lys | Asn |
| Trp | Ala | Thr 835 | Leu | Ala | Gln | Lys | Leu 840 | Gly | Leu | Gly | Ile | Leu 845 | Asn | Asn | Ala |
| Phe | Arg 850 | Leu | Ser | Pro | Ala | Pro 855 | Ser | Lys | Thr | Leu | Met 860 | Asp | Asn | Tyr | Glu |
| Val 865 | Ser | Gly | Gly | Thr | Val 870 | Arg | Glu | Leu | Val | Glu 875 | Ala | Leu | Arg | Gln | Met 880 |
| Gly | Tyr | Thr | Glu | Ala 885 | Ile | Glu | Val | Ile | Gln 890 | Ala | Ala | Ser | Ser | Pro 895 | Val |
| Lys | Thr | Thr | Ser 900 | Gln | Ala | His | Ser | Leu 905 | Pro | Leu | Ser | Pro | Ala 910 | Ser | Thr |
| Arg | Gln | Gln 915 | Ile | Asp | Glu | Leu | Arg 920 | Asp | Ser | Asp | Ser | Val 925 | Cys | Asp | Thr |
| Gly | Val 930 | Glu | Thr | Ser | Phe | Arg 935 | Lys | Leu | Ser | Phe | Thr 940 | Glu | Ser | Leu | Thr |
| Ser 945 | Gly | Ala | Ser | Leu | Leu 950 | Thr | Leu | Asn | Lys | Met 955 | Pro | His | Asp | Tyr | Gly 960 |
| Gln | Glu | Gly | Pro | Leu 965 | Glu | Gly | Lys | Ile |